United States Patent [19]

Wingard

[11] 4,421,129
[45] Dec. 20, 1983

[54] SHAPED ARTICLES FOR RAPID HAIR DRYING UTILIZING POLYMER BLENDS

[76] Inventor: Steve G. Wingard, 419 Lyndhurst Rd., Columbia, S.C. 29210

[21] Appl. No.: 407,590

[22] Filed: Aug. 12, 1982

[51] Int. Cl.³ .............................................. A45D 1/00
[52] U.S. Cl. ................................ 132/163; 132/11 R; 132/85; 132/120; 132/1 R; 132/9
[58] Field of Search ................... 132/163, 9, 11 R, 85, 132/120, 1 R; 527/300.14, 301, 302, 312, 313, 319, 315

[56] References Cited

U.S. PATENT DOCUMENTS

| | | | |
|---|---|---|---|
| 633,457 | 9/1899 | Hotze | 132/111 |
| 1,039,982 | 10/1912 | Maley | 132/110 |
| 1,147,681 | 7/1915 | Maley | 132/110 |
| 1,166,361 | 12/1915 | Grove | 132/110 |
| 1,169,028 | 1/1916 | Grove | 132/111 |
| 2,889,835 | 6/1959 | Hazzard | 132/109 |
| 2,895,487 | 7/1959 | Hazzard | 132/110 |
| 3,105,501 | 10/1963 | Scotti | 132/9 |
| 3,846,265 | 11/1974 | Yamaguchi et al. | 527/312 |
| 3,992,336 | 11/1976 | Faucher et al. | 260/17 R |
| 3,997,484 | 12/1976 | Weaver et al. | 260/17.4 GC |
| 4,013,086 | 3/1977 | Chmela | 132/110 |
| 4,018,729 | 4/1977 | Faucher et al. | 260/17 R |
| 4,076,663 | 2/1978 | Masuda et al. | 527/312 |
| 4,302,369 | 11/1981 | Elmquist | 260/17.4 GC |

OTHER PUBLICATIONS

"Preliminary Product Bulletin SGP TM 502S Water Soluble Polymer" General Mills Chemicals, Inc., (date unknown).
"Gel Sheets Produced by Hydration of Films from the Potassium Salt of Hydrolyzed Starch–Polyacrylonitrile Graft Copolymer" Weaver, Fanta, Bagley, Doane.
"Highly Absorbent Starch-Based Polymer" Weaver, Fanta, Doane, U.S. Department of Agriculture, Peoria, Ill. 61604.

Primary Examiner—C. Fred Rosenbaum
Assistant Examiner—Sherri Vinyard
Attorney, Agent, or Firm—Benoni O. Reynolds

[57] ABSTRACT

Shaped articles, such as hair brushes, combs and hair curlers, for rapid hair drying, molded in whole or in part of graft starch copolymer. Graft starch copolymers, such as base hydrolized starch-polyacrylonitrile, carbohydrate acrylic copolymer, modified carbohydrate derivatives, and combinations of polyacrylate and polyacrylamide, have superabsorbent properties. Graft starch copolymer is a blend of the natural polymer, starch, and synthetic polymers such as acrylamide and sodium or potassium acrylate. When used after a shower or after washing ones hair, these shaped articles, molded from graft starch copolymer, in accordance with the method of the present inventon, will absorb essentially all moisture from the hair, upon contact, in a matter of a few minutes.

8 Claims, 8 Drawing Figures

U.S. Patent   Dec. 20, 1983   4,421,129
FIG. 1.
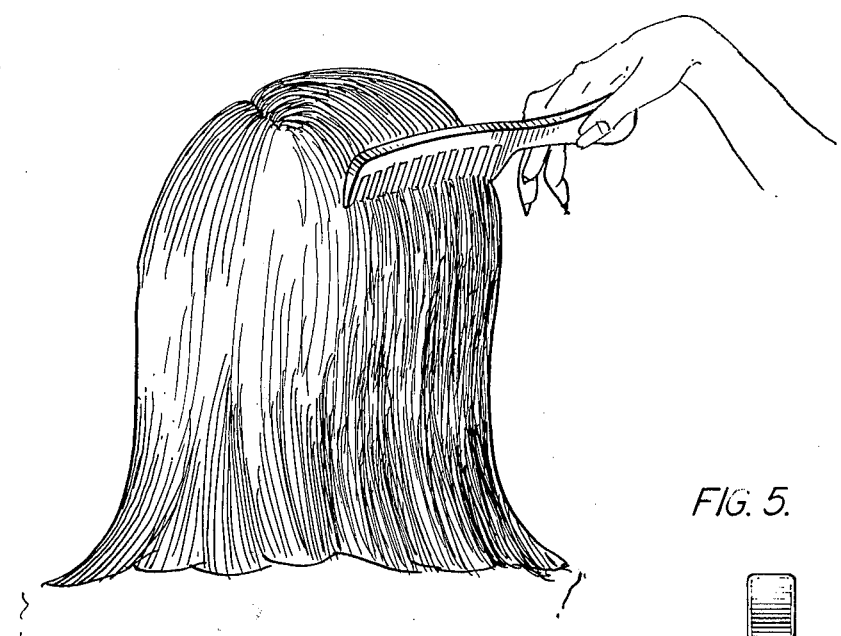
FIG. 5.
FIG. 2.
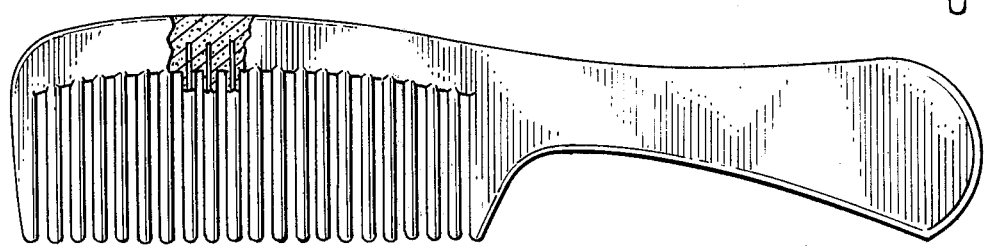
FIG. 3.
FIG. 6.   FIG. 7.
FIG. 4.
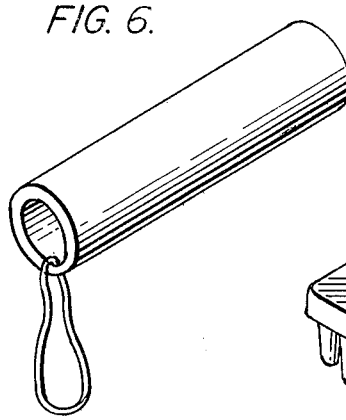
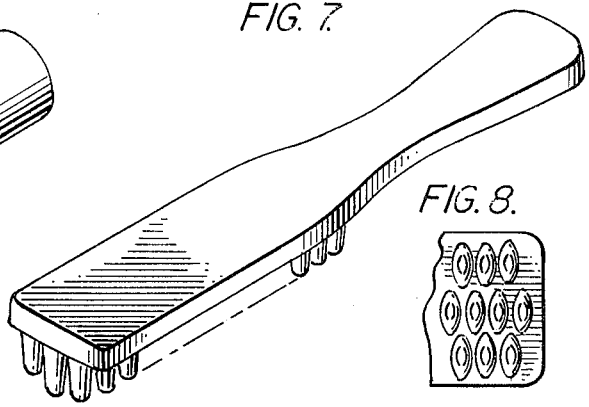
FIG. 8.
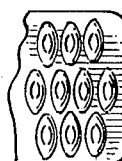

SHAPED ARTICLES FOR RAPID HAIR DRYING UTILIZING POLYMER BLENDS

BACKGROUND OF THE INVENTION (1) Field of Invention:

This invention relates to articles for rapid drying of hair and is particularly suited for combs, hair brushes and hair curlers.

(2) Description of Prior Art:

The oldest devices for "rapid" hair drying in the prior art dealt primarily with manual means, such as combs and brushes having removable inserts of water absorbent materials. Later devices have been addressed to delivering warm air, under pressure, utilizing heating elements coupled with electrically driven blower motors. Of course, the need for a power source is a disadvantage of the later art and limits the use of such devices to locations having electrical outlets. Another drawback of this later art is the time normally required to thoroughly dry ones hair, even with high powered blowers. Blow-dryers are expensive to purchase compared with manual devices and present maintenance problems unknown to the old art. Also, the high heat of blow-dryers may endanger the hair.

The very earliest hair drying combs had teeth composed of absorbent material, such as clay, asbestos or mineral wool, which were first heated by independent means and then passed through the hair to be dried. When the comb had become cooled and filled with moisture, it had to be heated again and used in the same manner, if needed. The moisture was taken up by capillary action and the materials used must have been capable of withstanding great heat.

Later devices were absorbent combs having plush stretched over a plurality of plates which engaged the hair of the user between the opposing surfaces of the absorbent material, thereby absorbing the moisture and surplus oils in the hair.

Another approach was a removable hair cleaning cover which slipped over the teeth of a hair comb like a slip cover over a chair. The comb body would be of wood and the absorbent material would be paper or cloth. The means for holding the absorbent material to the combs varied and some combs were held out only to be hair and scalp cleaners, rather than dryers. One means of holding the material was a comb split in half with the absorbent material held recessed between the two halves which formed a clamp when closed. Absorbent materials, such as paper pulp, were sometimes molded into teeth-like projections to form the core of hair cleaning combs which had recesses to accommodate the core material. When full of dirt and oils, the core would be discarded and replaced. In structure, some of these early hair and scalp cleaners took on the appearance of hair brushes but the technology was addressed to absorbing dirt and excessive oil from the hair.

The prior art overlaps into the hair drying, bleaching, and conditioning functions, as some of the devices having absorbent inserts could be used for both drying and hair conditioning. The primary application involving polymer moldings were shaped articles used for hair conditioning. Water solubility was looked upon as a means for conveying liquids (conditioners) to the hair rather than as a means for taking moisture from the hair. Water soluble polymers would be intertwined with water insoluble polymers, with the latter element to give structure and support to the water soluble element which would carry the conditioner to the hair. This same technique could be applied to the present invention but the water absorbent element would serve a different purpose, that of removing moisture quickly from the hair. The water insoluble polymer would merely give the shaped articles structure and strength.

Prior art known to this inventor includes the following U.S. Patent Numbers:

| | | |
|---|---|---|
| 633,457 | 9/1899 | Hotze |
| 1,039,982 | 10/1912 | Maley |
| 1,147,681 | 7/1915 | Maley |
| 1,166,361 | 12/1915 | Grove |
| 2,577,921 | 12/1951 | Samel |
| 2,785,693 | 3/1957 | Bova |
| 2,889,835 | 6/1959 | Hazzard |
| 2,895,487 | 7/1959 | Hazzard |
| 3,992,336 | 11/1976 | Faucher |
| 4,018,729 | 4/1977 | Faucher |
| 4,013,086 | 3/1977 | Chmela |

BRIEF SUMMARY OF THE INVENTION

The present invention is a shaped article from a group of shaped articles for rapid hair drying, such as a comb, hair brush or hair curler, molded under pressure, in whole or in part, of graft starch copolymer. Graft starch polymer is a blend of the natural polymer, starch, and a synthetic polymer such as acrylamide and sodium or potassium acrylate. The special properties of graft starch copolymer are imbibing up to 300 times its weight of water in a matter of minutes, while retaining its gross shape. The absorption is so rapid that little or no dimensional change takes place after the first ten minutes. Graft starch copolymer is available from a number of commercial sources, known as SGP 147 (Henkel Corporation), SGP 502S (General Mills Chemicals, Inc, now Henkel Corporation), and Water Lock (Grain Processing Corporation). Other applications are agricultural soil additives, absorbent softgoods such as sanitary pads, and hospital clean-up chores where superior fluid absorbency is required. The present invention is molded by placing the powdered form of graft starch copolymer under pressure while being held in a hardened steel mold at ambient temperature.

OBJECTIVES OF THE INVENTION

The objectives of the present invention are to provide reusable shaped articles for hair drying, which are:

(1) quick to absorb moisture from the hair to save the time and effort of the user (2) more simple and inexpensive to manufacture than devices known in prior art to perform the same function;

(3) compact in size and light in weight for ease of carrying by the user;

(4) unitary in design, requiring no replaceable absorbent elements or exchangeable parts, thus simplifying use and eliminating maintenance problems;

(5) easy to use and requiring no heat or electrical support;

(6) capable of styling as well as drying the hair; Other objectives and advantages of the present invention will become apparent during the course of the following detailed description.

BRIEF DESCRIPTION OF DRAWINGS

FIG. 1 is a perspective view of a person using a comb fabricated in accordance with the principles of the present invention.

FIG. 2 is a side view of a variation of a comb fabricated in accordance with the principles of the present invention.

FIG. 3 is a bottom view of the same variation.

FIG. 4 is a front end elevation view of the same variation.

FIG. 5 is a front end elevation view of a comb fabricated in accordance with the principles of the present invention.

FIG. 6 is a perspective view of a hair curler fabricated in accordance with the principles of the present invention.

FIG. 7 is a perspective view of a hair brush fabricated in accordance with the principles of the present invention.

FIG. 8 is fragmented bottom view of the same hair brush.

DETAILED DESCRIPTION OF THE PREFERRED EMBODIMENT OF THE INVENTION

The U.S. Department of Agriculture, as early as 1973, conducted studies of the unusual properties of the grafted starch copolymer, alkali hydrolized starch-polyacrylonitrile (H-SPAN) which had much potential in agriculture as a soil additive. Test showed that films formed from the potassium salt of H-SPAN (K-H-SPAN) by acqueous dispersion, after drying, could imbibe up to 300 times their weight in water in a matter of minutes, while retaining their gross shape. The absorption was so rapid that little or no dimensional change took place after the first ten minutes. The copolymer could be used either as a film coating on a substrate or as a particular solid held in place mechanically. Although ungrafted starch films imbibed water, the swelling was not of the magnetic observed with K-H-SPAN films. Total fluid absorbency was found to vary with fluid characteristics such as water hardness, ion content and pH. Maximum absorbency was achieved in pure water.

The present invention is a shaped article for rapidly drying hair, selected from the group consisting of combs, hair brushes and hair curlers, which are molded of graft starch polymer. The shaped article is molded by applying pressure of at least 200 Psi, at ambient temperature, to graft starch polymer held in a hardened steel mold, shaped to form the desired article. Ones hair can be rapidly dried by combing, brushing or curling the hair to be dried with the shaped article. The preferred graft starch copolymer is in powdered form, marketed in standard packaging of 50 pound multiwall bags selling from about $2.50 to $5.00 per pound depending upon the quantity purchased.

Several acceptable brands of graft starch copolymer are commercially available on the open market. A preferred brand would be SGP-147 which is marketed by the Henkel Corporation of Minneapolis, Minn. This category of SGP copolymer is described as being starch and a synthetic polymer of acrylamide and sodium acrylate or in the alternative, of acrylamide and potassium acrylate. They also offer SGP-502 and SGP 104 in both sodium salt and potassium salt form. The U.S. Department of Agriculture studies of 1973 indicated that the potassium salt version of graft starch polymer may be a preferred version for purposes of this invention. Experimental studies of the SGP graft starch copolymers showed them to be non-toxic although not approved for internal consumption. Proportions of starch and polymer in the product are approximately 2:3 while proportions of acrylate and acrylamide are approximately 3:1, The Specifications for SGP 147 are as follows: Typical Absorbency (determined by filtering a dispersion of SGP polymer and collecting unabsorbed fluid):

| Fluid | Volume Fluid Absorbed |
|---|---|
| pure water | 200–300 ml/g |
| 1.00% saline solution | 45–55 ml/g |
| Typical Analysis of Absorbent Powder | Values |
| Nitrogen | 2–3% |
| Volatiles | 5–10% |
| Ash (residue after burning) | 20–25% |
| Residual methanol | 1% |
| Trace Component Analysis | |
| Residual monomers | |
| Acrylates | 0.0150% (150 ppm) |
| Acrylamide | None detected* |
| Nitrile | None detected** |
| Cerium | 0.40–0.55% |

*Minimum level of detection 5 ppm
**Minimum level of detection .05 ppm

The above specification confirms the U.S. Department of Agriculture summary of their Dec. 11, 1973 report in which they said:

"The solid water-insoluble sorbent that swells in water is a base-hydrolized starch-polyacrylonitrile graft copolymer in which the nitrile functionality has been converted to a mixture of carboxamide and alkali metal carboxylate."

Stiefel Laboratories, Inc., who use "Supersorb" in some of their talc powders, describe graft starch copolymer as carbohydrate acrylic copolymer. They state "Supersorb" is a modified carbohydrate derivative with exceptional absorbent qualities.

Grain Processing Corporation of Muscatine, Iowa, market a graft starch copolymer which they describe as being of polyacrylate and polyacrylamide. The product is not irritating to the skin nor is it a skin sensitizer.

Obviously, other similar graft starch copolymers may be satisfactory for use in the present invention. The above review of known commercial sources was not intended to limit the scope of graft starch copolymers which fulfill the objectives of the present invention.

Any fabricating method known to those skilled in the art can be used for molding the shaped articles. Either compression or injection molding yields satisfactory results and temperatures are not critical. Molding a shaped article, for combing, brushing or curling hair, by applying pressure of at least 200 Psi, at ambient temperature, to graft starch copolymer held in a hardened steel mold, is disclosed as the preferred method of producing the present invention. Pressures up to 40,000 Psi have yielded satisfactory results. Immediately after molding, the shaped article can be used for combing, brushing or curling the hair to be dried. The hydroscopic property of graft starch copolymer is such that it absorbs moisture very rapidly, reaching more than 50% of its absorbent capacity in 30 seconds. After use, the shaped article contracts to its original dimensions and regains its absorbent capacity by merely letting it dry at room (ambient) temperature. The simplest version of the shaped article is to mold it entirely of graft starch copolymer. A variation of the present invention would be the comb, wherein only the teeth of the comb are fabricated from graft starch copolymer. The remainder of the comb would be fabricated from some other material, such as insoluble polymer. Similarly, another variation would be the hair brush, wherein only the bristles of the hair brush are fabricated of graft starch copolymer. The remainder of the hair brush would be fabricated from some other material, such as an insoluble polymer. A third variation would be the hair curler, wherein only the surface of the hair curler is fabricated from graft starch copolymer. The remainder of the hair curler would be fabricated from some other material, such as an insoluble polymer.

EXAMPLE

A hardened steel mold is prepared for a hair brush 8 9/10 inches long by 4 inches wide and ½ inches thick at the base. Approximately ½ of the length of the hair brush has slightly concave edges and the end is rounded to form a handle. Extending upwardly from the base of the remaining ½ of the hair brush are 43 bristles ¾ inches in height, shaped like elliptical cones, 15 bristles forming the middle row of bristles and 14 bristles forming each of the two outside rows. Each bristle is ¼ inches across the narrow part of the ellipse at the top and is ⅝ inches across the narrow part of the ellipse at the bottom where the bristle is affixed to the base of the hair brush. The side surface of the cone-like bristles form a 20% plane from the vertical. The design of this shaped article, shown only as an example, provides for the uniform expansion which occurs in the hygroscopic process as the hair brush drys and styles the hair. SGP 147, the graft starch copolymer marketed by the Henkel Corporation as a powder, is injected into the hardened steel mold by injection until the mold is filled completely. 2000 Psi of pressure is then applied to the graft starch copolymer in the mold at ambient temperature. After 30 seconds, the shaped article is removed from the hardened steel mold and tested by stroking hair moistened by a shampoo or a shower.

Although the present invention has been described in its preferred form fabricated from preferred brands of graft starch copolymer with a certain degree of particularlity, it is understood that the present disclosure of the preferred forms and known commercial sources of graft starch copolymer have been made only by way of example and that numerous changes may be resorted to without departing from the spirit and scope of the present invention.

I claim:
1. A shaped article for rapidly drying hair, comprising:
   rigid means engaging the hair, for absorbing water therefrom, said rigid means made from a hydrolized graft starch copolymer selected from the group consisting of:
   starch, acrylamide and sodium acrylate, or
   starch, acrylamide and potassium acrylate, or
   starch, polyacrylate and polyacrylamide,
   whereby water is absorbed from the hair by hydroscopic action of said graft starch copolymer.
2. The article of claim 1 wherein said rigid means is a comb fabricated entirely of said graft starch copolymer.
3. The article of claim 1 wherein said rigid means is a comb wherein only the teeth of said comb are fabricated from said graft starch copolymer.
4. The article of claim 1 wherein said rigid means is a hair brush fabricated entirely of said graft copolymer.
5. The article of claim 1 wherein said rigid means is a hair brush wherein only the bristles of said hair brush are fabricated of said graft starch copolymer.
6. The article of claim 1 wherein said rigid means is a hair curler fabricated entirely of said graft starch copolymer.
7. The article of claim 1 wherein said rigid means is a hair curler wherein only the surface of said hair curler is fabricated of said graft starch copolymer.
8. The process of fabricating the rigid means of claims 1 through 7, wherein said rigid means is fabricated by applying pressure, at ambient temperature, to said graft starch copolymer held in a hardened steel mold.

* * * * *